United States Patent [19]

Navarre

[11] Patent Number: 4,578,986

[45] Date of Patent: Apr. 1, 1986

[54] GAS ANALYZER FOR DRY/DUSTY KILNS

[75] Inventor: Anatole J. Navarre, Houston, Tex.

[73] Assignee: Champion International Corporation, Stamford, Conn.

[21] Appl. No.: 628,632

[22] Filed: Jul. 6, 1984

[51] Int. Cl.[4] .................... G01N 1/24; G01D 18/00
[52] U.S. Cl. ............................... 73/1 G; 73/863.24; 73/863.83
[58] Field of Search ............... 73/1 G, 863.81, 863.83, 73/863.86, 863.11, 863.12, 863.23, 863.24, 23

[56] References Cited

U.S. PATENT DOCUMENTS

| | | | |
|---|---|---|---|
| 3,559,491 | 2/1971 | Thoen | 73/863.24 |
| 3,924,442 | 12/1975 | Kerho et al. | 73/1 G |
| 4,004,882 | 1/1977 | Byrne et al. | 73/863.23 X |
| 4,047,437 | 9/1977 | Brooks | 73/863.23 |
| 4,059,019 | 11/1977 | Wurster et al. | 73/863.81 |
| 4,094,187 | 6/1978 | Navarre, Jr. | 73/1 G |
| 4,150,495 | 4/1979 | Stern | 73/1 G X |
| 4,161,883 | 7/1979 | Laird et al. | 73/862.24 |
| 4,279,142 | 7/1981 | McIntyre | 73/1 G |
| 4,481,833 | 11/1984 | Bajek | 73/863.81 X |
| 4,485,684 | 12/1984 | Weber et al. | 73/863.86 X |

FOREIGN PATENT DOCUMENTS

| | | | |
|---|---|---|---|
| 951467 | 3/1964 | United Kingdom | 73/863.12 |
| 1275905 | 6/1972 | United Kingdom | 73/863.12 |

Primary Examiner—Jerry W. Myracle
Assistant Examiner—Tom Noland
Attorney, Agent, or Firm—Evelyn M. Sommer; John H. Mulholland; William W. Jones

[57] ABSTRACT

A system for the analysis of gas samples from a dry and dusty environment, such as the interior of a lime kiln, includes a probe which extends relatively far into the kiln, to avoid the adverse effect on the measurements of extraneous, i.e., "tramp", air which may leak into the kiln. A sample of the gas is drawn through an isolation tube which extends from the probe chamber in a direction for sample flow opposite to the flow of gases in the kiln. The sample is passed through a filter, within the probe chamber; pumped to a conditioning system, in which the sample gas is cleaned and cooled; and then pumped to gas analysis cells for the analysis of the individual gases.

The probe chamber is mounted at the end of a support pipe which carries a first tube, connected to the filter. This pipe serves as a path to introduce purge air for the filter and also calibration gases for test purposes. The actual gas sample is withdrawn through an innermost pipe which terminates just upstream of the inlet of the filter. A third tube, connects directly into the probe chamber, and not through the filter, and through which purge air or span gases may be pumped.

12 Claims, 4 Drawing Figures

GAS ANALYZER FOR DRY/DUSTY KILNS

BACKGROUND OF THE INVENTION

This invention relates to gas analyzing systems and more particularly to such systems which may be used to analyze samples of gas drawn from dry and dusty environments, such as lime kilns.

One problem with prior gas analysis systems used to analyze the gases in a hot, dry and dusty environment, such as lime kiln, is that the systems became inaccurate, over time, as their probe lines became clogged with dust. Prior systems, because their lines were clogged, had a slower response time. Inaccuracies also arose because of the adverse effect of "tramp" air, which is air that flows into the kiln through seal leaks, incompletely closed doors and other accidental causes. Such tramp air may have a disproportionate effect on measurements made by the system especially those involving oxygen.

One type of previously disclosed gas monitoring system is shown in the inventor's prior U.S. Pat. No. 4,094,187 ('187 patent) entitled "Stack Gas Analyzing System With Calibrating/Sampling Feature", incorporated by reference herein. In U.S. Pat. No. 4,094,187 patent it is explained that "real-time" gas analyzer uses pipes to convey the gas to a nearby analyzer to permit their immediate analysis and the adjustment of process parameters based upon that analysis. Such rapid adjustments may prevent the exhaust of unacceptable levels of pollutants, and may prevent injury to the kiln and/or associated equipment. In U.S. Pat. No. 4,094,187 patent the calibration gases are supplied to the analyzers through the same gas path used by the samples of the effluent.

OBJECTIVES AND FEATURES OF THE INVENTION

It is an objective of the present invention to provide a gas monitoring system for dry, dusty and hot environments such as lime kilns, which system will be relatively accurate to permit more accurate control of the fuel/air ratio in order to conserve fuel and maintain an efficient and safe operation of the kiln's boiler.

It is a further objective of the present invention to provide such a monitoring system which tests itself for accuracy using commercially available span gases, i.e., commercially available calibration gases.

It is a further objective of the present invention to provide such a monitoring system which will monitor oxygen ($O_2$) combustible gases (methane, etc.), carbon monoxide (CO) and carbon dioxide ($CO_2$).

It is a further objective of the present invention to provide such a monitoring system which is relatively fast in the time required for its self-calibration, for example, less than two minutes, in order to use relatively less of its span gases for calibration.

It is a further objective of the present invention to provide such a monitoring system which will be fully automatic in operation, under microprocessor control, so that its calibration, blanking and purging will be automatically commenced, controlled and terminated without attention from an operator.

It is a further objective of the present invention to provide such a monitoring system which is designed to help prevent the entry of dust, along with the gas to be sampled, into the monitoring system, so that the sample which is tested may be relatively "unconditioned", i.e., not cleaned prior to analysis.

It is a further objective of the present invention to provide such a monitoring system which will not be adversely affected in the accuracy of its measurements by the presence of hydrogen sulfide or humidity in the sample.

SUMMARY OF THE INVENTION

In accordance with the present invention, a system for real-time analysis of effluent gas is provided. The system includes a probe which extends relatively far into the kiln; for example, it extends 14 feet, to avoid the adverse effect on the measurement of "tramp" air, i.e., extraneous air which may leak into the kiln. The effluent gas to be analyzed is hot and moist. A sample is taken, through the probe and the moisture and heat removed by cooling the sample. Some of the gas sample, now at room temperature (70° F.) is pumped into an oxygen analyzer. Other portions of the dried gas sample are pumped to other analyzers. Preferably the "span gases", i.e., the commercially obtained gases used for calibration of the system, are nitrogen, oxygen and methane, depending on the connected analyzers.

The probe is mounted at the end of a probe support which is an elongated support pipe. The gas sample is obtained through an isolation tube which leads to the probe chamber and which is pointed for sample flow opposite in direction to the flow of gas. Two pipes, suspended within the support pipe, are connected to the probe chamber. One of the pipes carries a tube through which the effluent gas samples are drawn and the second pipe carries air to purge the probe chamber and the calibration span gases.

BRIEF DESCRIPTION OF THE DRAWINGS

Other objectives and features of the present invention will be apparent from the following detailed description, which should be taken in conjunction with the accompanying drawings.

In the drawings.

DETAILED DESCRIPTION OF THE INVENTION

Figure 1:
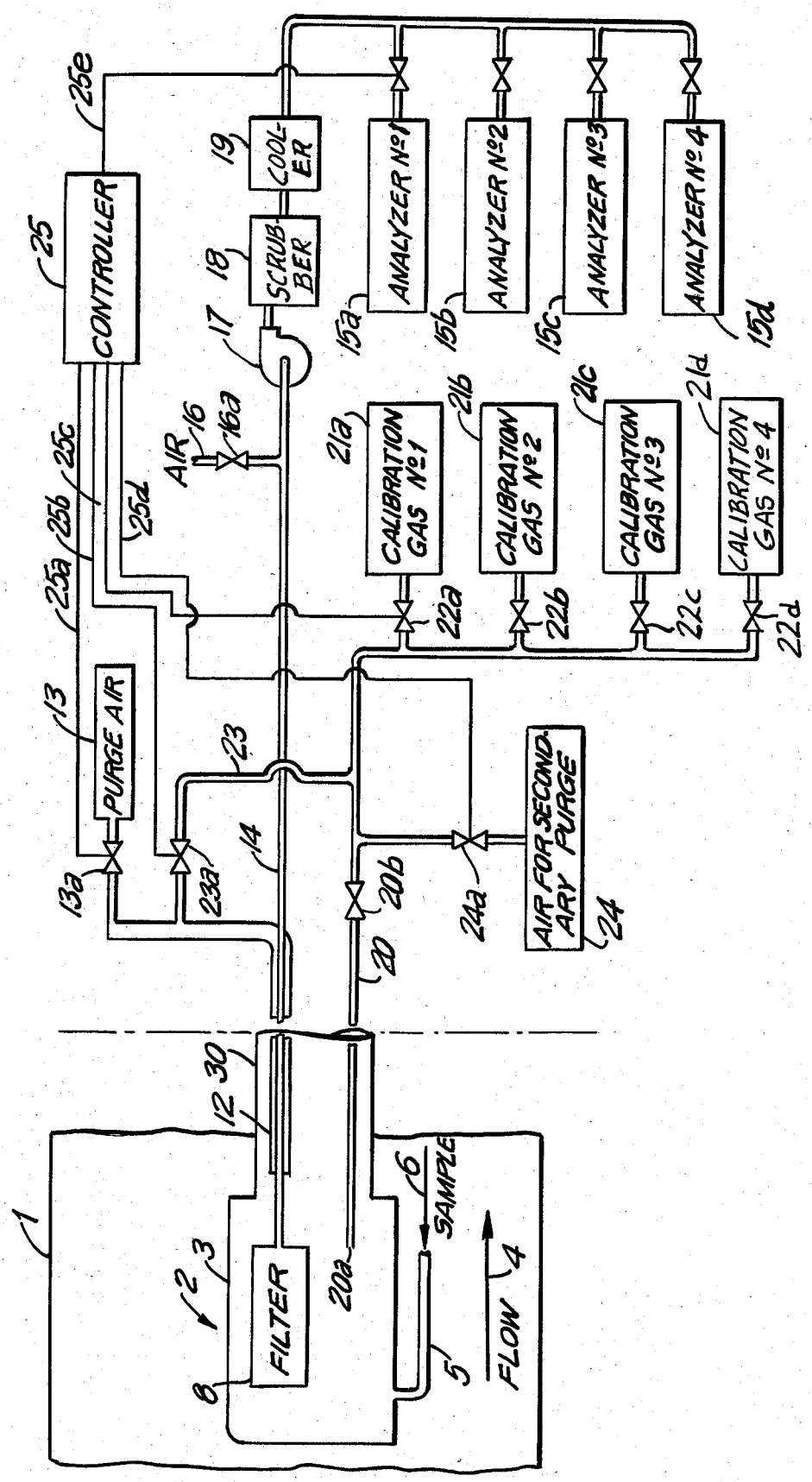
FIG. 1 is a block diagram of the gas analyzing system of the present invention.

As shown in FIG. 1, the effluent gas analyzing system of the present invention is for analyzing gases in a dry dusty environment, such as that found in a lime kiln 1. The gases that are desired to be tested are oxygen ($O_2$), methane (combustibles), carbon dioxide and carbon monoxide.

Figure 2:
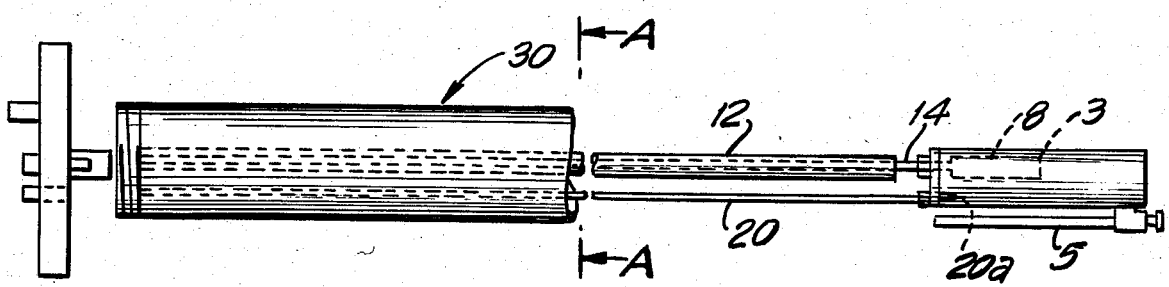
FIG. 2 is a side view, partly in section, of the probe for use in the system of FIG. 1.

The stack probe 2, shown in detail in FIG. 2, extends into the kiln 1. The dusty flue gases within kiln 1 flow in the direction of arrow 4. The sample 6 is taken through the isolation tube 5, which points for sample flow 6 in the opposite direction from flow 4. The sample 6 passes into the interior of the probe chamber 3.

The direction and size of the isolation tube 5 prevents the pulsations in pressure in the effluent gas flow from affecting the gas pressure within the probe chamber 3. This isolation from the effect of pulsation permits a low flow of "span" gases, i.e., calibration gas, during the calibration cycle. The amount of flow of span gas may be regulated so that it is slightly in excess of the sampling rate (the rate of flow of the gas sample).

The change in direction of 180°, of the flow of sample 6 from the flow 4, prevents the heavier dust particles from entering the probe chamber 3 with the sample. That change in direction effectively separates the heavier particles, which are carried past the isolation tube 5 due to their higher inertial energy. The probe chamber 3 is mounted on the end of the pipe 12. The pipe 12 leads through control valve 13a to a source of atmospheric purge air 13.

An unconditioned sample of the gases from within kiln 1 is pumped from probe chamber 3 through filter 8 and exhausted through tube 14, which tube is carried within the pipe 12. The sample passes through sample pump 17 to the conditioning system. The conditioning system includes scrubber 18. From scrubber 18 the gas can be passed through cooler 19, to remove its moisture. The gas sample, when it exits from cooler 18, is at room temperature (70° F.), or lower. The gas is then pumped and divided so that portions are pumped to oxygen ($O_2$) analyzer 15a and to three other analyzers. The three analyzers are analyzer 15b for combustibles (methane), analyzer 15c for carbon monoxide (CO) and analyzer 15d for carbon dioxide.

A second pipe 20, with a blocking valve 20b, within and leading from probe chamber 3, leads to the source of the calibration gases 21. That source 21 consists of standard compressed calibration gases (span gases) which, for example, are oxygen 21a, methane 21b, carbon dioxide 21c, and carbon monoxide 21d. The calibration gases, in pressurized cylinders, are controlled by the respective valves 22a, 22b, 22c and 22d.

Preferably the valves, such as 22a-22d, and the exhaust pipe are electrically operated and controlled from a digital micro-processor flow control computer 25. The lines 25a-25e leading to and from computer 25, are electrical control lines. Only representative electrical control lines are shown, for the purpose of clarity of the illustration. However, preferably all the valves are electrically controlled by the controller 25.

Preferably, the control computer 25 operates valve 13a once an hour, to purge the filter 8 of the probe chamber 3 with air to clean the filter. The entire unit is preferably calibrated once a day, automatically by the control computer 25. Such calibration may take from 2-5 minutes, and tests have shown that a calibration period of 2½ minutes is satisfactory.

A tube 23 leads from the pipe 12 to the calibration gases 21. The control valve 23a is normally closed but is opened to permit the flow of calibration gases through pipe 12 and into the probe chamber 3. This will put the entire probe system under positive gas pressure in order to test for air in-flow leaks. Such leaks, unless detected and halted, would result in inaccurate measurements.

The source of pressurized air 24, which is connected to tube 20 through control valve 24a, is used as a secondary air purge. The secondary air purge preferably is automatically cycled so that the air from air source 24 may clear out dust from the probe chamber 3. The secondary air, along with the dust, will be expelled through the isolation tube 5.

The problem of tramp air, i.e., leakage of air into the sample system, is especially serious when the oxygen analyzer is used, as even small air leaks can lead to inaccurate oxygen measurements. The alternative calibration mode is used to detect such leaks. In the alternative calibration mode, the valve 23a is opened and the calibration gases from compression sources 21a-21d pass through pipe 12 and the filter 8 into the probe chamber 3. The gas pressurizes the sample system and any leaks may be detected.

Figure 3:
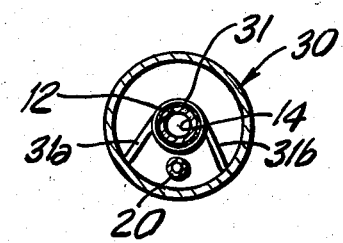
FIG. 3 is a cross-sectional view, taken along line A—A of FIG. 2, looking in the direction of the arrows.
Figure 4:
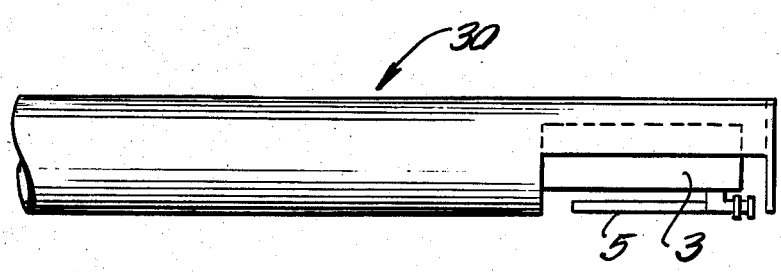
FIG. 4 is a side view of the free end of the probe.

As shown in FIGS. 2 and 3, the isolation tube 5, which is preferably a ½-inch pipe, is attached near the free end of the probe chamber 3. The pipe 20 is preferably a ¼-inch (diameter) pipe and is connected so that its exit orifice 20a is within the probe chamber 3. The tube 14 consists of a ⅜-inch tubing inside of a ½-inch pipe. The pipe 12 ends 2 inches before the probe chamber. The ½-inch pipe (of tube 14) has its exit orifice within filter 8 and the tube 14 lies almost entirely within the pipe 12. Preferably pipe 12 is a 1-inch pipe. The pipe 12 is centered within the support pipe 30 by strap metal supports 31. Each support 31 has two legs 31a and 31b. The support 31 is welded to the pipe 12. A single support 31 is within the support pipe 30 to hold the pipe 12. The support pipe 30 extends along the entire length of the probe until the rear face of the probe chamber and, at its opposite end, extends through the dust chamber wall into the kiln proper. Alternatively, the support pipe 30 may be mounted on a blind flange fixed to a kiln wall. The probe chamber 3 is supported by the tube 20, tube 14 and pipe 30; the main support for the probe chamber being the tube 14. Preferably the support pipe 30 is a 6-inch (diameter) pipe.

What is claimed is:

1. A gas analyzer system for use in dry and dusty environments, wherein gas samples are withdrawn by the system from within a chamber, the system comprising:
   a plurality of gas analyzer cells, a plurality of sources of calibration gases and a source of purge air, said cells and sources being located outside of the chamber environment;
   a probe support means including a support pipe extending sufficiently far into the chamber to substantially avoid the effect of tramp air on the measurments, the support pipe having a free end in the chamber;
   a probe chamber fixed near the free end of the support pipe;
   an isolation tube means fixed to the probe chamber to bring sample gas into the probe chamber and a filter means within the probe chamber to filter the gas samples;
   a first pipe means, to selectively pressurize the system, which conducts gas and air from the sources of calibration gas and source of purge air to the probe filter, the first pipe means being laid for a substantial extent of its length within said support pipe;
   a second pipe means laid for a substantial extent of its length within said support pipe to conduct calibration gases and purge air from the said sources to the probe chamber; and
   a sample tube means laid for a substantial extent of its length within said support pipe to conduct gas samples from the filter to the gas analyzer celis.

2. A gas analyzer system as in claim 1 wherein said sample tube means is a tube laid for a substantial part of its length with said first pipe means.

3. A gas analyzer system in claims 1 or 2 and further including a series of metal supports internal to the support pipe and positioned internally along its length to support said first pipe means away from the internal wall of the support pipe.

4. A gas analzyer system as in claim 1 and further including a gas conditioning means between said sample tube means and said gas analyzer cells, said conditioning means including gas scrubber means to remove dust and cooling means to remove humidity.

5. A gas analyzer system in claim 1 wherein said gas analyzer cells are analyzers for oxygen, carbon monoxide, carbon dioxide, and methane.

6. A gas analyzer system as in claim 1 and further including electrically operated valves for each of the sources of calibration gases, the gas analyzer cells and the source of purge air, and an automatic controller means to operate the system on a timed sequence of steps by controlling the said valves.

7. A gas analyzer system for use in dry and dusty environments in which a gas flows in one direction in a chamber, comprising:
 a plurality of gas analyzer cells, a plurality of sources of calibration gases and a source of purge air;
 a probe support means including a support pipe extending sufficiently far into the chamber to substantially avoid the effect of tramp air on the measurements, the support pipe having a free end in the chamber;
 a probe chamber fixed near the free end of the support pipe;
 an isolation tube fixed to the probe chamber which extends from the probe chamber in a direction opposite to the flow of gas;
 a filter within the probe chamber;
 a first tube within the probe support means which leads from the source of purge air and the source of calibration gases to within the filter to selectively pressurize the system;
 a second tube within the probe support means which leads from the source of purge air and the sources of calibration gases to the probe chamber; and
 a third tube within the probe support means which leads from within the filter to the gas analyzer cells to extract gas samples from within said probe chamber.

8. A gas analyzer system as in claim 7 wherein said third tube is positioned within said first tube.

9. A gas analyzer system as in claim 7 wherein said first tube is held away from the internal walls of the support pipe by a series of one or more metal supports.

10. A gas analyzer system as in claim 7 and further including a gas conditioning means between said third tube and said gas analyzer cells, said conditioning means including a gas scrubber means to remove dust and a cooling means to lower the temperature of the gas and remove humidity.

11. A gas analyzer system as in claim 7 wherein said gas analyzer cells are analyzers for oxygen, carbon monoxide, carbon dioxide and methane.

12. A gas analyzer system as in claim 7 and further including an automatic controller means to operate the system on a timed sequence of steps, and electrically operated valves controlled by said controller means and positioned at the orifices of each source of calibration gas, of each analyzer cell, and of the source of purge air.

* * * * *